United States Patent
Luetje et al.

(10) Patent No.: US 10,780,242 B2
(45) Date of Patent: Sep. 22, 2020

(54) PARTIAL RELAXATION ENCLOSURE WITH PADDED ISOLATION AND AMBIENT DAMPENER PANELS

(71) Applicants: Julia Helena Luetje, Leawood, KS (US); Susan Allison Bernstein, Leawood, KS (US)

(72) Inventors: Julia Helena Luetje, Leawood, KS (US); Susan Allison Bernstein, Leawood, KS (US)

( * ) Notice: Subject to any disclaimer, the term of this patent is extended or adjusted under 35 U.S.C. 154(b) by 117 days.

(21) Appl. No.: 16/167,098

(22) Filed: Oct. 22, 2018

(65) Prior Publication Data
US 2019/0117932 A1  Apr. 25, 2019

Related U.S. Application Data (60) Provisional application No. 62/575,216, filed on Oct. 20, 2017.

(51) Int. Cl.
*A61M 21/00* (2006.01)
*A61M 21/02* (2006.01)

(52) U.S. Cl.
CPC ......... *A61M 21/0094* (2013.01); *A61M 21/02* (2013.01); *A61M 2021/0027* (2013.01); *A61M 2021/0044* (2013.01)

(58) Field of Classification Search
CPC .. A61M 21/00; A61M 21/02; A61M 21/0094; A61M 2021/0027; E04B 1/8218; E04B 1/99; E04B 1/994
See application file for complete search history.

(56) References Cited

U.S. PATENT DOCUMENTS

| | | | | |
|---|---|---|---|---|
| 3,014,477 | A * | 12/1961 | Carlin | A61M 21/00 600/27 |
| 3,085,568 | A * | 4/1963 | Whitesell | A61G 13/009 601/55 |
| 6,446,751 | B1 * | 9/2002 | Ahuja | A47H 23/02 181/280 |
| 7,044,083 | B2 * | 5/2006 | Farmer | A01K 1/0254 119/474 |
| 2013/0079584 | A1 * | 3/2013 | Armbruster | B68G 7/00 600/28 |
| 2016/0073801 | A1 | 3/2016 | Shin et al. | |
| 2016/0168847 | A1 | 6/2016 | Saunier | |
| 2017/0318975 | A1 * | 11/2017 | Schwab | A61B 17/0218 |

FOREIGN PATENT DOCUMENTS

| | | | | |
|---|---|---|---|---|
| CA | 2578639 | * | 7/2008 | ........... E04B 1/8218 |
| FR | 1342264 | | 9/1962 | |

OTHER PUBLICATIONS

International Search Report and Written Opinion received in connection with PCT/US18/567912 dated Feb. 5, 2019, 14 pages.

* cited by examiner

*Primary Examiner* — Carrie R Dorna
(74) *Attorney, Agent, or Firm* — Hovey Williams LLP (57) ABSTRACT

An enclosure including one or more panels that together define a header and two generally opposing sides. The header and two generally opposing sides define a reclining pocket for receiving a body part of an individual. Each of the one or more panels includes a cushion layer and a sound absorbing layer having an interior side. The cushion layer is disposed along and at least partly overlaps the interior side of the sound absorbing layer. The sound absorbing layer exhibits a greater sound absorption coefficient than the cushion layer.

20 Claims, 9 Drawing Sheets

PARTIAL RELAXATION ENCLOSURE WITH PADDED ISOLATION AND AMBIENT DAMPENER PANELS

CROSS-REFERENCE TO RELATED APPLICATION

The present application claims the benefit of, identically-titled U.S. Provisional Application Ser. No. 62/575,216, filed Oct. 20, 2017, the entirety of which is hereby incorporated by reference herein.

BACKGROUND

Conventional pads for providing comfort to reclining individuals—such as pillows—include a cushion and, optionally a removable, washable covering. Typically placed under the head or back, the cushion of such pads resiliently supports and distributes the weight of an individual's body to enhance the comfort of reclining and reduce soreness.

An improved device for increasing the level of comfort experienced by reclining individuals is needed.

SUMMARY OF THE INVENTION

One embodiment of the invention is an enclosure including one or more panels that together define a header and two generally opposing sides. The header and two generally opposing sides define a reclining pocket for receiving a body part of an individual. Each of the one or more panels includes a cushion layer and a sound absorbing layer having an interior side. The cushion layer is disposed along and at least partly overlaps the interior side of the sound absorbing layer. The sound absorbing layer exhibits a greater sound absorption coefficient than the cushion layer.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

An enclosure 10 constructed in accordance with embodiments of the present invention is illustrated in FIGS. 1-5. The enclosure 10 includes a header panel 12 attached to first and second side panels 14, 16. The header panel 12 and side panels 14, 16 together define a reclining pocket 18 for receiving a body part of an individual. For example, the individual may place head, shoulders and an upper portion of the torso into the reclining pocket (see FIG. 3), resting on an underlying flooring or similar surface. Remaining ensconced in the enclosure 10 may enhance the individual's comfort in several ways, according to the description of preferred embodiments provided herein.

The enclosure 10 is shown in a deployed configuration in FIGS. 1-3, and in a stowed configuration in FIGS. 4-5, as discussed in more detail below. The exemplary deployed enclosure 10 forms a U-shaped pocket 18. However, it is foreseen that enclosures in other substantially concave shapes may form reclining pockets without departing from the spirit of the present invention.

Each of the header panel 12 and side panels 14, 16 includes a sound absorbing layer 20 having a substantially planar interior side 22 and a cushion layer 24 generally disposed along and at least partly overlapping the interior side 22. For example, the cushion layer 24 may comprise a memory foam, and the sound-absorbing layer 20 may comprise a sound reducing foam. The layers 20, 24 may be joined together using fasteners or adhesives, and/or may be held together by other elements of the enclosure 10 (see discussion of casing 29 below). In the illustrated embodiment, the cushion layer 24 substantially entirely overlaps and is co-extensive with the interior side 22 of the sound absorbing layer 20. One of ordinary skill will appreciate that layers that are not substantially co-extensive are also within the scope of the present invention.

In the preferred embodiment, each of the header panel 12 and side panels 14, 16 also includes a second sound absorbing layer 26. The sound absorbing layer 20 includes a substantially planar exterior side 28. The illustrated second sound absorbing layer 26 is disposed along and at least partly overlaps the exterior side 28. The layers 20, 26 may be joined together using fasteners or adhesives, and/or may be held together by other elements of the enclosure 10 (see discussion of casing 29 below). In the illustrated embodiment, the second sound absorbing layer 26 substantially entirely overlaps and is co-extensive with the exterior side 28 of the sound absorbing layer 20. One of ordinary skill will appreciate that layers that are not substantially co-extensive are also within the scope of the present invention. It is also foreseen that sound absorbing layers may swap interior/exterior positions without departing from the spirit of the present invention.

Each of the sound absorbing layers 20, 26 may include porous, membrane (panel) and/or resonance absorbers comprising material(s) such as: acoustic fiberglass, acoustic foam, mass loaded vinyl, acoustic fabric, acoustic cotton, cork, rubber, fiberboard, slag wool or glass silk, hardwood, mineral wool and/or the like. In the preferred embodiment, the sound absorbing layers 20, 26 exhibit sound absorption properties differently across frequency ranges. For example, the sound absorbing layer 20 may include a sound absorbing material optimized for mid- to high-frequency absorption (such as a porous absorber comprising open cell rubber foams, melamine sponges or the like). In turn, the second sound absorbing layer 26 may include a sound absorbing material optimized for low-frequency absorption (such as a mineral wool or the like). The combined sound absorbing layers 20, 26 may thereby dampen/absorb sound across a wide range of frequencies for improved isolation of the reclining pocket 18 and comfort of the individual.

In a preferred embodiment, the second sound absorbing layer 26 may be of sufficient thickness and composition to exhibit a sound absorption coefficient at or above five-tenths (0.5) for sound waves having a frequency within a low range of, for example, one hundred and twenty-five to two hundred and fifty Hertz (125-250 Hz). Further, the preferred sound absorbing layer 20 may be of sufficient thickness and composition to exhibit a sound absorption coefficient at or above nine-tenths (0.9) for sound having a frequency within a range higher than the low range. For example, the high range may be above five hundred Hertz (500 Hz) and at or below five thousand Hertz (5,000 Hz). The sound absorption coefficients for such materials may be measured in isolation for each layer using established procedures such as ISO® Standard 354 (1985)—Acoustics—Measurement of Sound Absorption in a Reverberation Room, propagated by the International Organization for Standardization as of the initial filing date of this disclosure.

One of ordinary skill will appreciate that one or more sound absorbing layers may have varying sound absorption properties across various sound frequency ranges within the scope of the present invention. One of ordinary skill will also appreciate that the thickness and composition of the selected layer(s) may be varied to achieve the preferred sound absorption characteristics outlined herein. Moreover, it is foreseen that various bass trap structures may be incorporated into an exterior face of a low-frequency absorption layer—and overlying casing may be omitted so as not to cover such structure(s) and/or layer(s)—without departing from the spirit of the present invention. Panels comprising a single homogenous layer of material are also within the scope of the present invention.

The enclosure 10 also includes a casing 29. The casing 29 envelops and encloses the layers 20, 24, 26, and may substantially restrict or prevent the ingress of contaminants (such as fluids, dusts, etc. from the surrounding environment) into the layers 20, 24, 26. The casing 29 may comprise typical upholstery material(s)—such as linen, leather, cotton, wool, cotton blend, vinyl and/or the like—of low to moderate thickness (e.g., one sixteenth to one eighth inches thick (1/16- to 1/8 in.)). Preferably, the casing 29 comprises materials of a given composition and thickness so as to exhibit a sound absorption coefficient of less than five tenths (0.5) at all frequencies between two hundred and fifty and two thousand Hertz (250-2,000 Hz), which is the typical range of frequencies output by a mid-range speaker (discussed in more detail below). However, it is foreseen that various types and thicknesses of flexible coverings may be utilized without departing from the spirit of the present invention.

The casing 29 may also contribute to the stability of the enclosure 10, for instance by compressing the layers 20, 24, 26 together to improve structural integrity and/or may render fasteners and/or adhesives between two or more of the layers 20, 24, 26 unnecessary. One of ordinary skill will appreciate that casing may be omitted from one or more surfaces of cushion and/or sound absorption layers within the scope of the present invention.

The cushion layer 24 preferably exhibits a hardness and sound absorption coefficient that are each less than those of the mid- to high-frequency absorption layer 20. Owing to its primary function of improving the physical cushioning offered to the individual along the interior of the enclosure 10, the cushion layer 24 may include less dense—and, correlatively, less hard—materials, which may correspond to lesser sound absorption at high frequencies. The layers 20, 24, 26 therefore provide a combination of improved physical comfort and broad-spectrum sound absorption.

It should be noted here that the hardness of the layers 24, 20 may be measured in isolation for each layer using established procedures such as ASTM® D5672/D5672M-15 Standard Test Method for Testing Flexible Cellular Materials Measurement of Indentation Force Deflection Using a 25-mm [1-in.] Deflection Technique, propagated by the American Society for Testing and Materials Corporation as of the initial filing date of this disclosure. One of ordinary skill will appreciate that materials of various hardness and thickness may form a cushion layer without departing from the spirit of the present invention.

It should also be noted that the layers 20, 24, 26 and casing 29 are illustrated with relatively sharp external edges. However, it is foreseen that such edges may be more rounded for improved comfort without departing from the spirit of the present invention.

Figure 4:
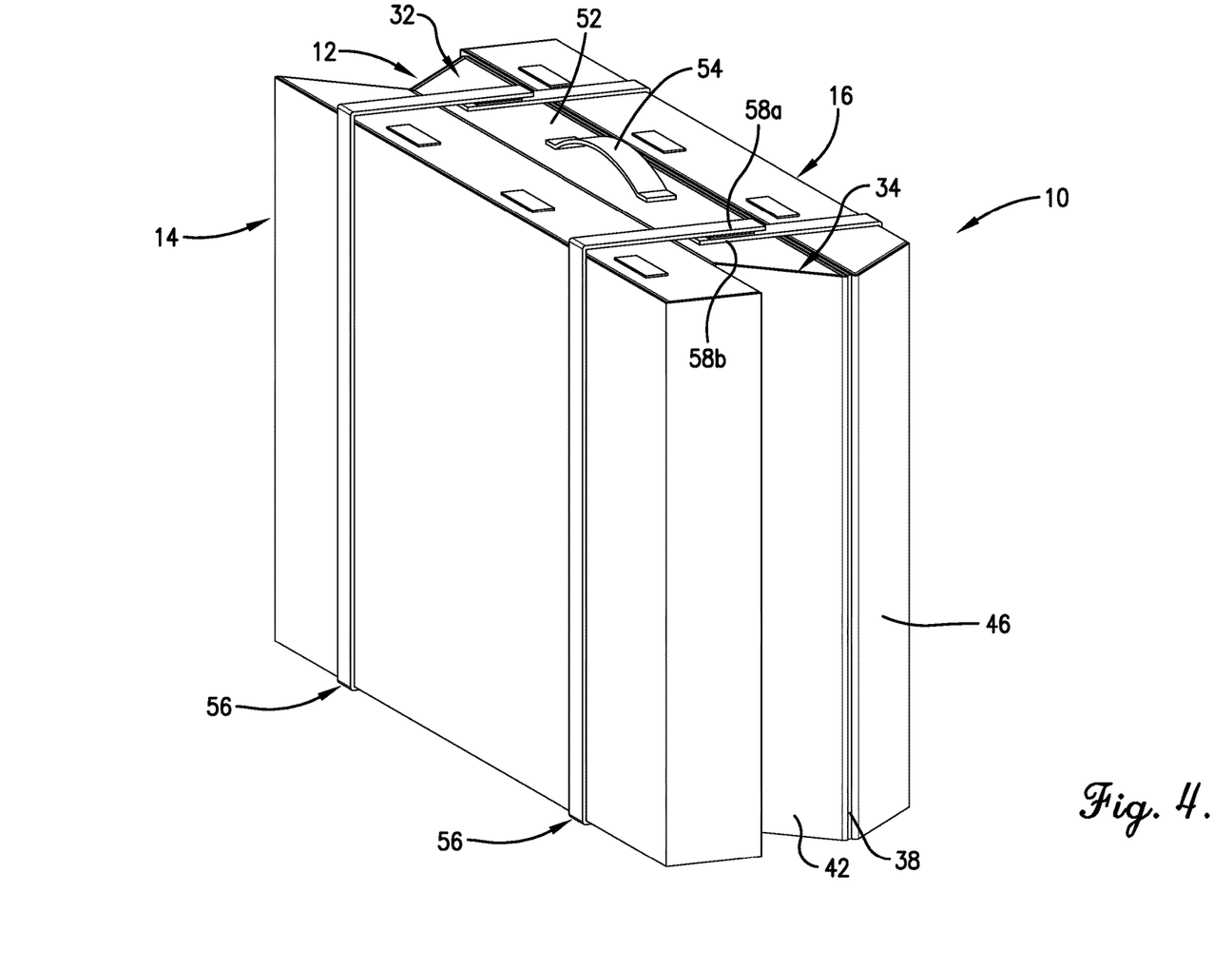
FIG. 4 is a perspective view of the enclosure of FIGS. 1-3, illustrating the enclosure in a stowed configuration.
Figure 5:
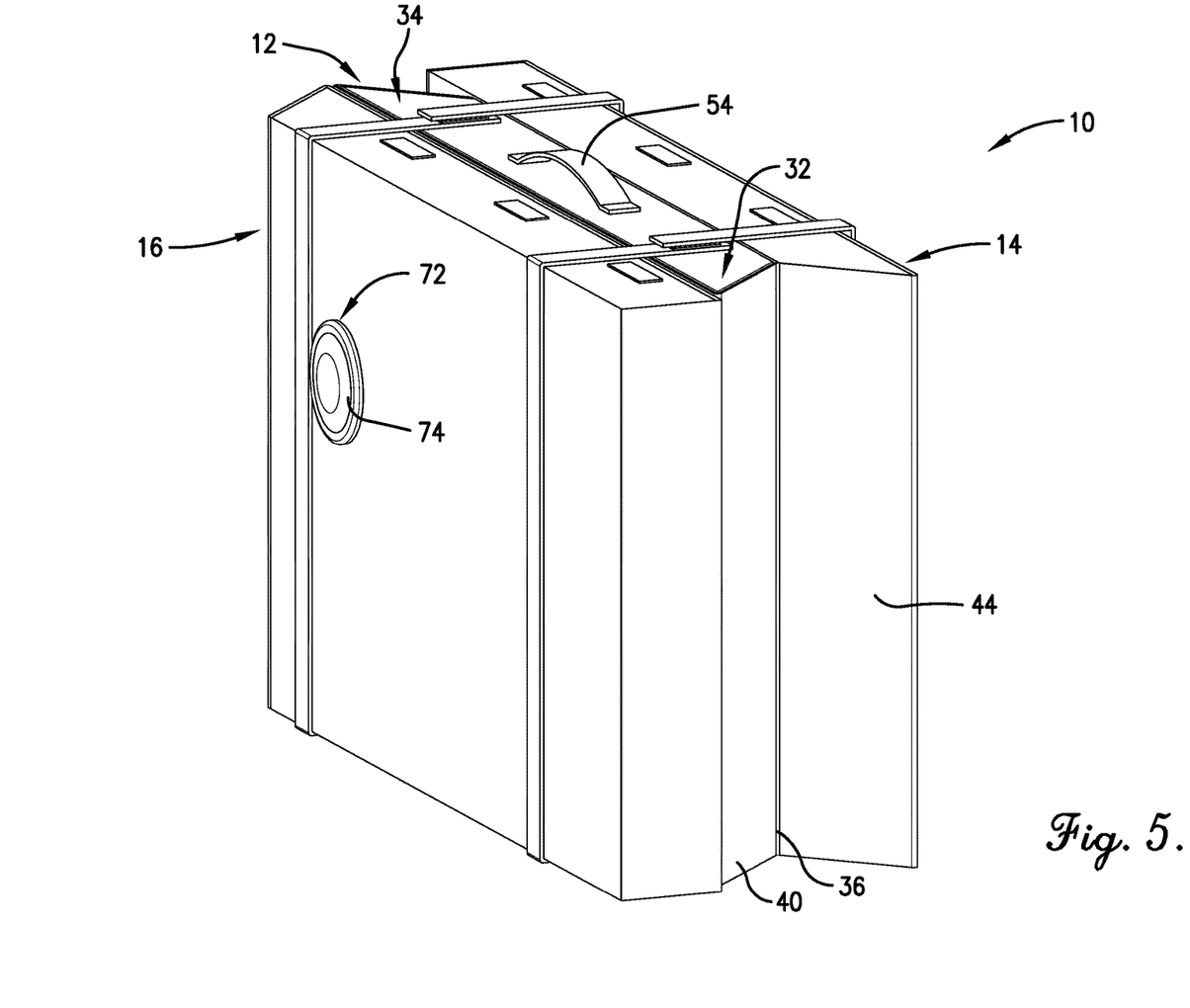
FIG. 5 is a perspective view of the enclosure taken from an opposite angle from FIG. 4 to show opposite side and end faces of the panels.

Turning to FIGS. 4-5, the side panels 14, 16 are respectively attached to opposite sides 32, 34 of the header panel 12 at hinges 36, 38. The illustrated hinges 36, 38 comprise strips of the material of the casing 29. The hinges 36, 38 extend along joints between and rotatably interconnect respective side panels 14, 16 and the header panel 12. It is foreseen that a variety of hinge types may be used without departing from the spirit of the present invention. One of ordinary skill will also appreciate that an enclosure comprising a substantially continuous or monolithic panel forming a concave shape—and therefore omitting hinges, a discontinuous series of interconnected panels, and/or the like—is within the scope of the present invention. It is also foreseen that an enclosure may comprise a plurality of panels detachably (e.g., via hook and loop fastener(s)) or permanently (e.g., via stitching) fixed together, and that the panels may or may not rotate or swing relative to one another, without departing from the spirit of the present invention.

Preferably, the header panel 12 includes oblique side faces 40, 42 respectively extending along opposite sides 32, 34 of the header panel 12. (See FIGS. 4-5) Moreover, the respective side panels 14, 16 include oblique end faces 44, 46 configured to complementarily abut corresponding side faces 40, 42. Abutment of each of end faces 44, 46 to a corresponding side face 40, 42 restricts rotation of each side panel 14, 16 about the header panel 12 to a single direction when collapsing the enclosure 10 into a stowed configuration as seen in FIGS. 4-5, with the side panel 14 rotating in the opposite direction to the side panel 16.

Figure 1:
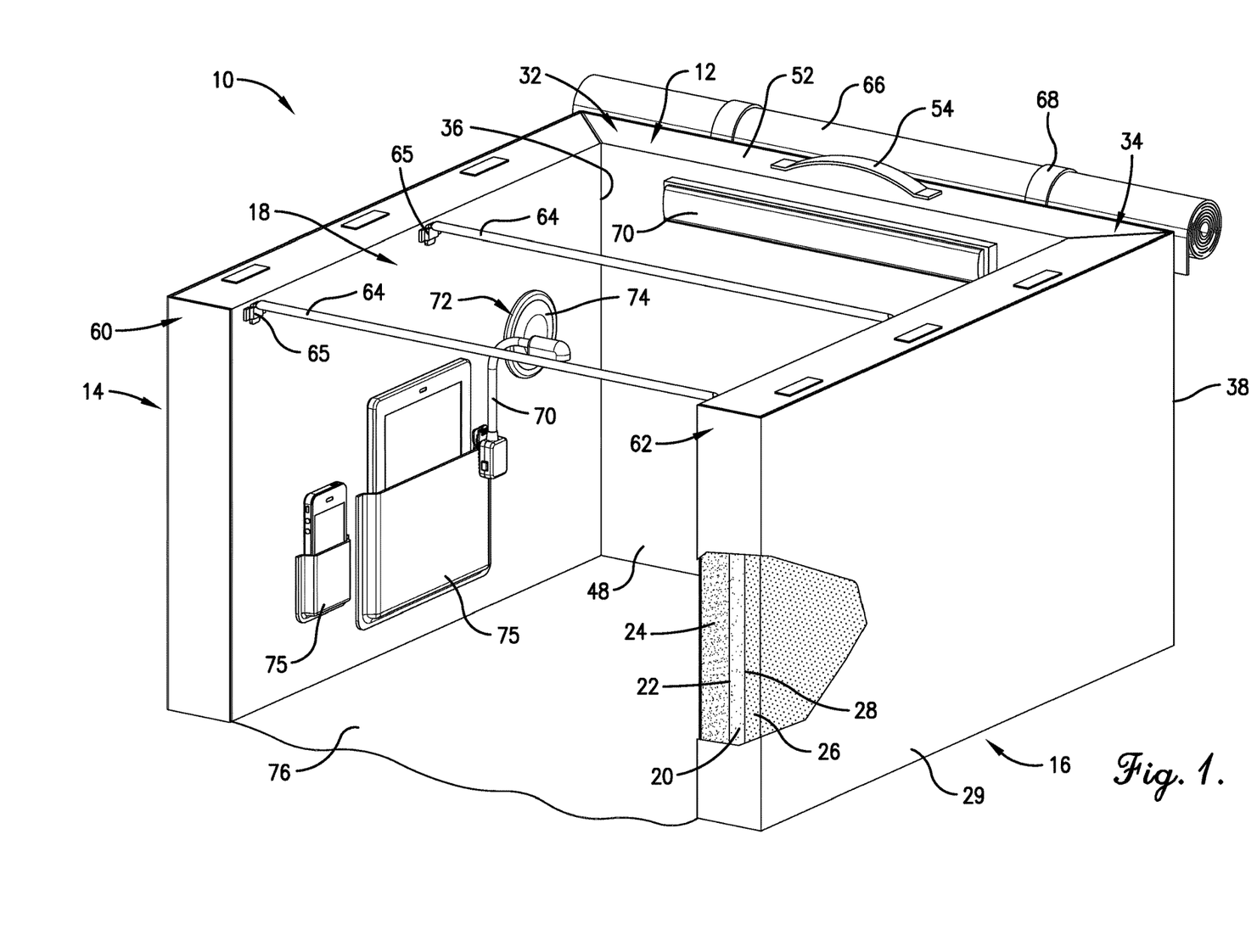
FIG. 1 is a perspective view of an enclosure constructed according to a first embodiment of the present invention, the enclosure having a side panel sectioned to reveal cushion and sound absorbing layers.
Figure 2:
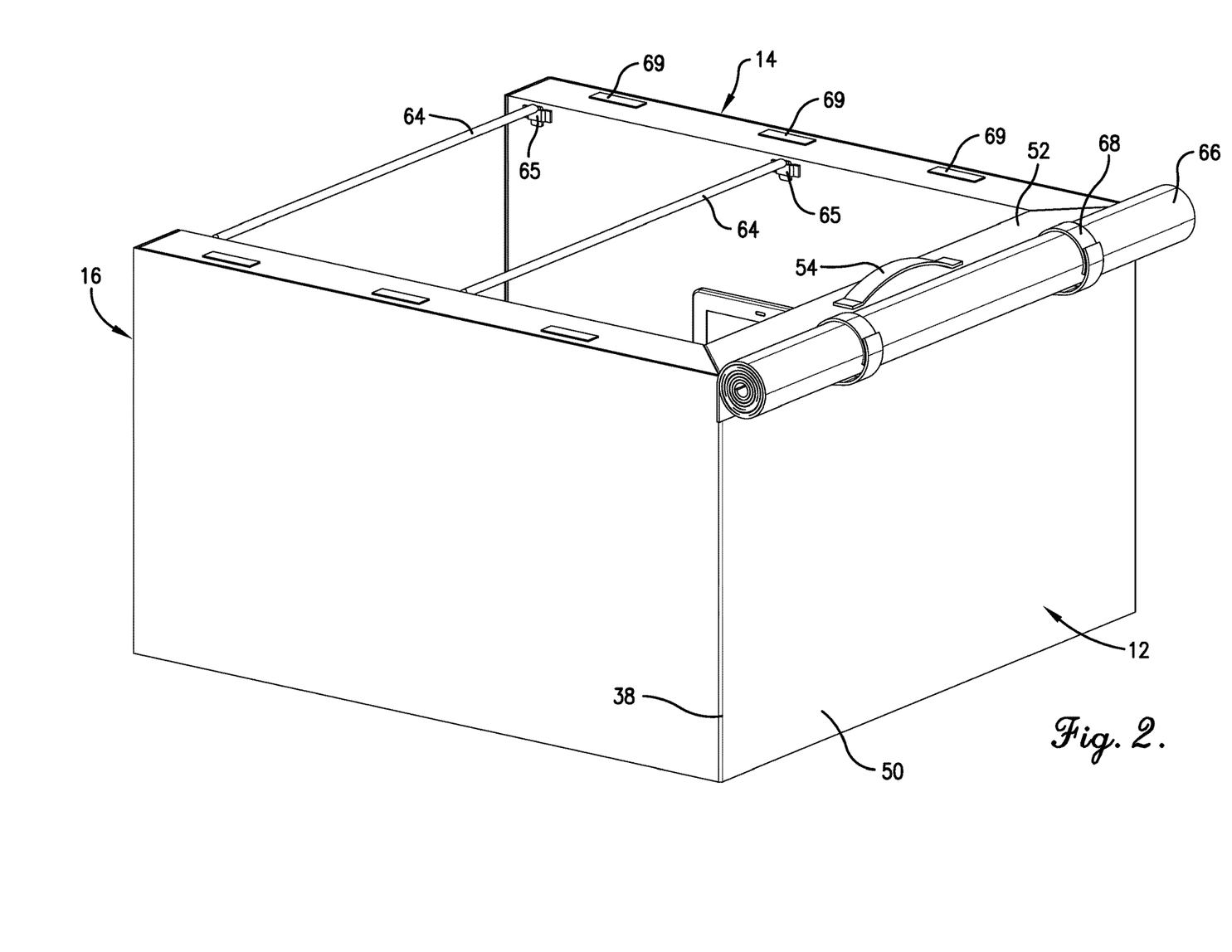
FIG. 2 is a perspective view of the enclosure taken from an opposite angle from FIG. 1 to show exterior faces of the side panel and a header panel.
Figure 3:
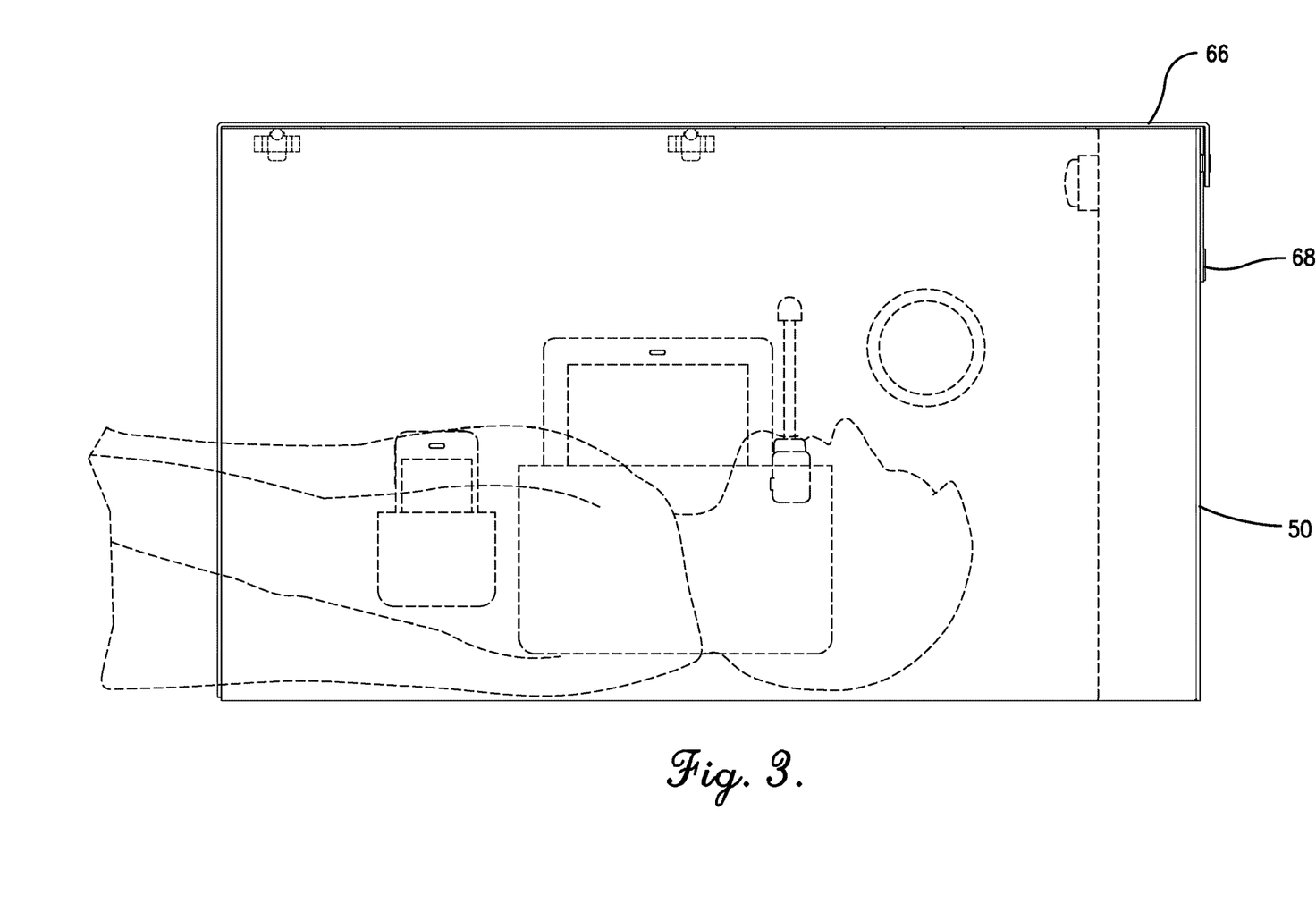
FIG. 3 is a side view of the enclosure of FIGS. 1-2, illustrating an individual reclining in a reclining pocket of the enclosure.

More particularly, the header panel 12 includes an interior face 48 (see FIG. 1) and an exterior face 50 (see FIG. 2). In a stowed configuration, the side panels 14, 16 are rotated about the header panel 12 so that each abuts one of the interior and exterior faces 48, 50. In the illustrated embodiment, the side panel 14 abuts the interior face 48 and the side panel 16 abuts the exterior face 50. Preferably, the hinge 36 extends along an edge between the interior face 48 and the side face 40 along the side 32, and the hinge 38 extends along an edge between the exterior face 50 and the side face 42 along the side 34, in keeping with the direction of panel rotation discussed above. In this manner, the side panel 14 is restricted to collapsing into abutment against the interior face 48 (only) and the side panel 16 is restricted to collapsing into abutment against the exterior face 50 (only) for stowing. This may help prevent breakage and/or attempts at folding into incorrect stowage configurations by the individual. It is foreseen that an enclosure may be configured for collapsing panels in varying orientations without departing from the spirit of the present invention.

The header panel 12 may also include a surface 52 that is exposed when the side panels 14, 16 are in a stowed configuration. In the illustrated embodiment, the surface 52 is a top surface of the header panel 12, though another exposed surface is also within the scope of the present invention (as described in connection with alternative embodiments below). A handle 54 may be fixed to the surface 52 for carrying the enclosure 10 in a stowed configuration and/or relocating the enclosure in a deployed configuration.

The enclosure 10 may also include at least one stowing strap 56 having free ends 58a and 58b. Stowing straps 56 may be fixed to one or more surfaces of the panels 12, 14, 16 (not shown). The free ends 58a and 58b may respectively include fasteners—such as snap fasteners, hook and/or loop fastener(s) sold under the mark VELCRO® by Velcro BVBA Private LLC, and/or other fasteners—for removable attachment to one another. More particularly, the free ends 58a and 58b may be wrapped about the panels 12, 14, 16 and fixed to one another to retain the stowed configuration.

Returning to FIGS. 1-3, showing enclosure 10 in a deployed configuration, the panels 14, 16 may include top portions 60, 62. The U-shape of the deployed panels 12, 14, 16 may be retained with at least one rigid rod 64 having ends fixed respectively to the top portions 60, 62. More particularly, the top portions 60, 62 may include bases 65 (e.g., comprising loops sewn to the casing 29 or the like) for removably securing the ends of the rigid rods 64 to the top portions 60, 62. Thus secured, the panels 14, 16 may be substantially restricted from rotating about the header panel 12 unless and until the rods 64 are removed from the top portions 60, 62.

The enclosure 10 may also include a cover 66. The cover 66 may be detachably fixed to the header panel 12, as discussed in more detail below. The cover 66 may comprise any textile, such as a cloth or woven fabric. Preferably, the cover 66 comprises a material having insulative properties, such as a blanket of relatively significant thickness. The cover 66 may be retracted (e.g., rolled or collapsed) away from the top portions 60, 62 when not in use. The enclosure 10 may also include straps or tabs 68 fixed adjacent the exterior face 50 of the header panel 12. The tabs 68 may encircle and secure the cover 66 when retracted (see FIG. 1), for example by employing fasteners (not shown) embedded in opposite free ends that are thereby fixed together. When deployed across the top portions 60, 62, the cover 66 may be supported on the rods 64. Top margins or surfaces of the side panels 14, 16 may also include hook and/or loop fasteners 69 fixed to the side panels 14, 16 and removably attaching to the cover 66 when deployed over the side panels 14, 16. It is foreseen that a cover and/or tabs may be otherwise positioned and/or excluded without departing from the spirit of the present invention.

The enclosure 10 may further include one or more electronic devices integral therewith and/or attached thereto. For example, the enclosure 10 may include electric lights 70 clamped to the casing 29, at least partially embedded within one or more of the layers 20, 24, 26, removably fixed to the panel(s) 12, 14, 16 (e.g., via hook and/or loop fasteners), and/or otherwise fixed to the enclosure 10. The electric light(s) 70 may be light-emitting diode (LED) light(s). For another example, the enclosure 10 may include audio speakers 72 (such as mid-range speakers) at least partly embedded in one or more of the layers 20, 24, 26. The speakers 72 may be fixed to one or more of the layers 20, 24, 26 via adhesive(s) and/or fastener(s) (not shown). The casing 29 may cover interior faces or sides 74 of the speakers 72 and, in such cases, preferably comprises a material exhibiting a low sound absorption coefficient (e.g., less than five tenths (0.5)) at all frequencies between two hundred and fifty and two thousand Hertz (250-2,000 Hz), inclusive. One of ordinary skill will appreciate that a casing may not cover an interior face of a speaker and that the speaker may be otherwise disposed along and/or fixed to one or more panels within the scope of the present invention. The casing may be removeable from an interior face of a speaker within the scope of the present invention. It is also foreseen that an enclosure may include more or fewer speakers without departing from the spirit of the present invention.

The enclosure 10 may still further include at least one pocket 75 comprising, for example, additional material of the casing 29 sewn to an interior surface of the casing 29. Each pocket 75 may be appropriately sized to receive one or more electronic devices, such as smart watches, smart phones, personal digital assistants (PDAs), tablets, palmtop or laptop computers, notebooks, netbooks, smart glasses, wearable electronics, or the like. One of ordinary skill will appreciate that pockets may be formed by other materials, may be otherwise fixed to an enclosure, and/or may be sized for various other uses such as receiving books or the like, within the scope of the present invention.

Each electronic device of the enclosure 10 (e.g., light(s) 70 and/or speakers 72) may be powered using alternating current (AC) power provided via conventional cabling or the like (not shown) and supplied by one or more power sources. Also or alternatively, the electronic device(s) may be powered using direct current (DC) power provided by one or more batteries (not shown) of the enclosure 10. For example, such batteries may share housing with and/or be internal to the device(s) and/or be otherwise disposed along the enclosure 10, with electrical communication with the device(s) being provided via cabling or the like. Moreover, the speakers 72 may be configured for wired or wireless communication—e.g., utilizing signals and/or data that comply with communication standards such as cellular 2G, 3G, or 4G, IEEE 802.11 standard (such as WiFi), IEEE 802.16 standard (such as WiMAX), Bluetooth™, or combinations thereof—with one or more audio source devices (not shown) for providing an audio signal to the speakers 72.

The enclosure 10 may yet still further include a floor covering 76 underlying the panels 12, 14, 16 (see FIG. 1). The floor covering 76 may comprise any textile, such as a cloth or woven fabric, and may provide additional padding to improve the comfort of a reclining individual within the reclining pocket 18. The floor covering 76 may optionally be fixed to one or more of the panels 12, 14, 16 (attachment points not shown), and may be folded within the enclosure 10 in a stowed configuration. One of ordinary skill will appreciate that a floor covering may be otherwise disposed along and/or fixed to one or more panels within the scope of the present invention.

The enclosure 10 may include additional, fewer, or alternate components and/or functionality, including that discussed elsewhere herein.

FIGS. 6, 7 and 8-9 respectively illustrate three alternative embodiments of the present invention. In each case, it is initially noted that, with certain exceptions to be discussed below, many of the elements of enclosures 600, 700, 800 of the three alternative embodiments are the same as or very similar to those described in detail above in relation to the enclosure 10 of the first embodiment. Therefore, for the sake of brevity and clarity, redundant descriptions and numbering will be generally avoided here. Unless otherwise specified, the detailed descriptions of the elements presented above with respect to the first embodiment should therefore be understood to apply at least generally to each of the three alternative embodiments as well.

Figure 6:
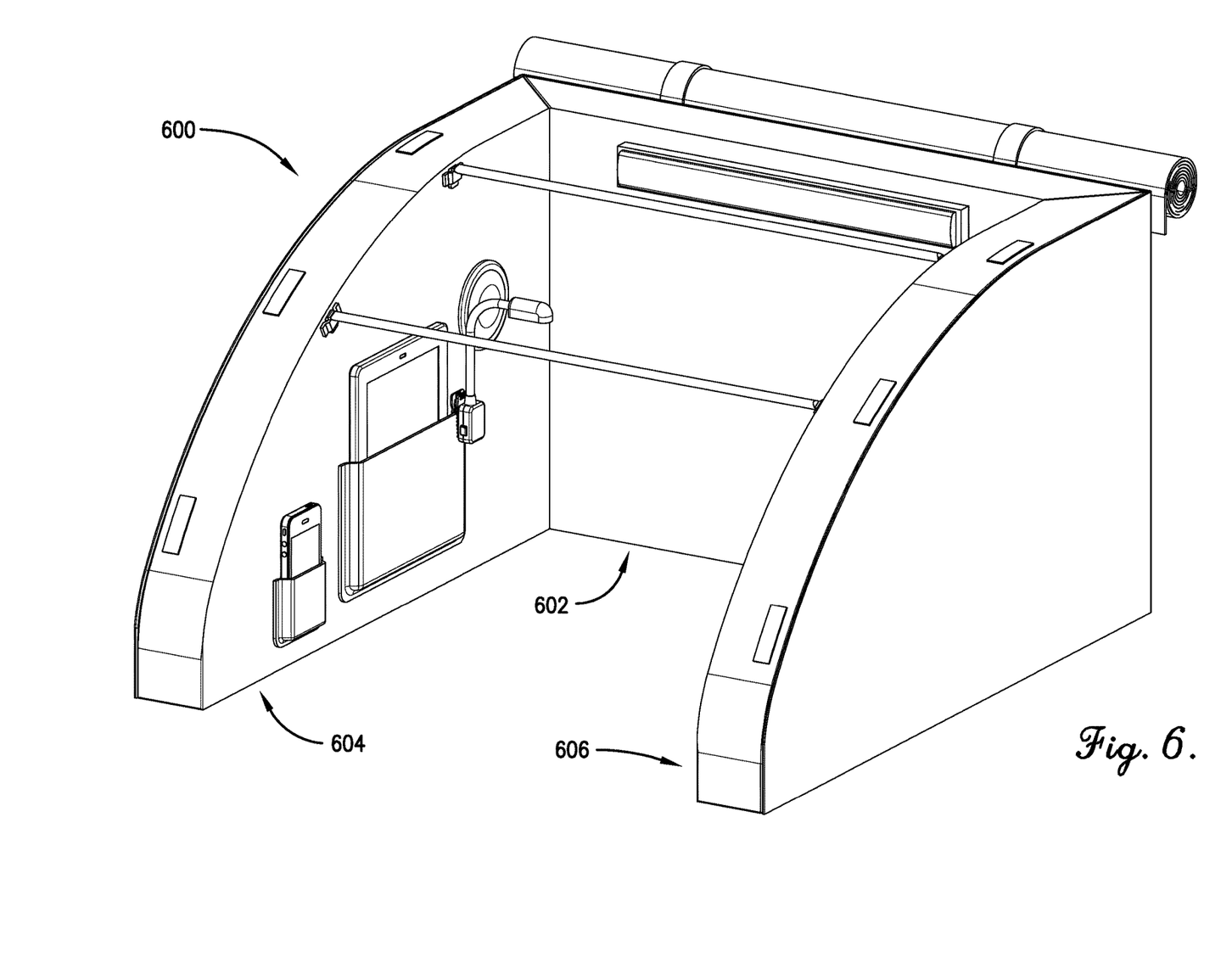
FIG. 6 is a perspective view of an enclosure constructed according to a second embodiment of the present invention.
Figure 7:
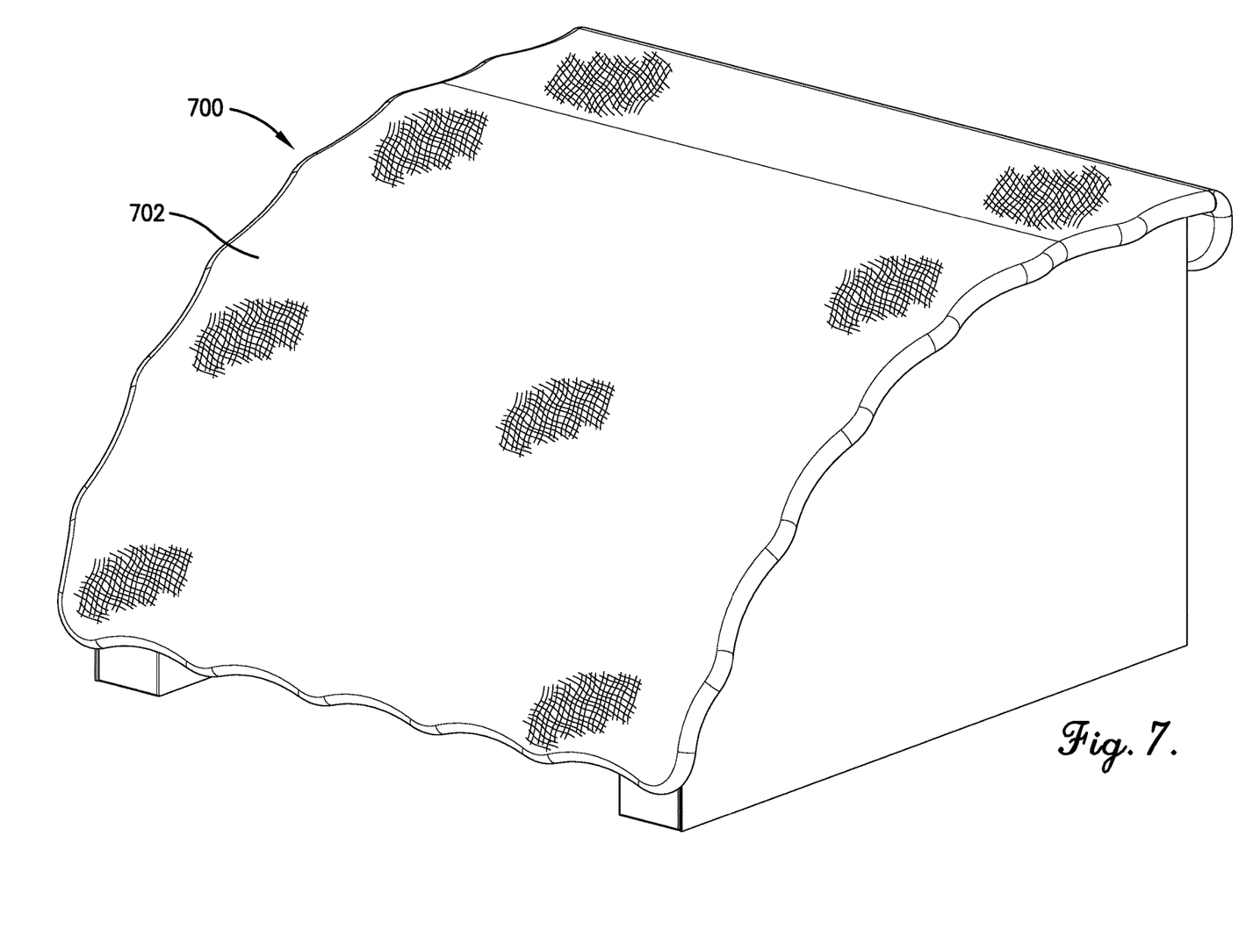
FIG. 7 is a perspective view of an enclosure constructed according to a third embodiment of the present invention.

Turning more particularly to FIG. 6, a second embodiment comprising enclosure 600 includes a header panel 602 and side panels 604, 606. The side panels 604, 606 present an arcuate top margin and a different side profile from that of the enclosure 10. Turning to FIG. 7, a third embodiment comprising enclosure 700 closely resembles the enclosure 600, except that a thickened cover 702 extends over the top margin of the enclosure 700.

Figure 8:
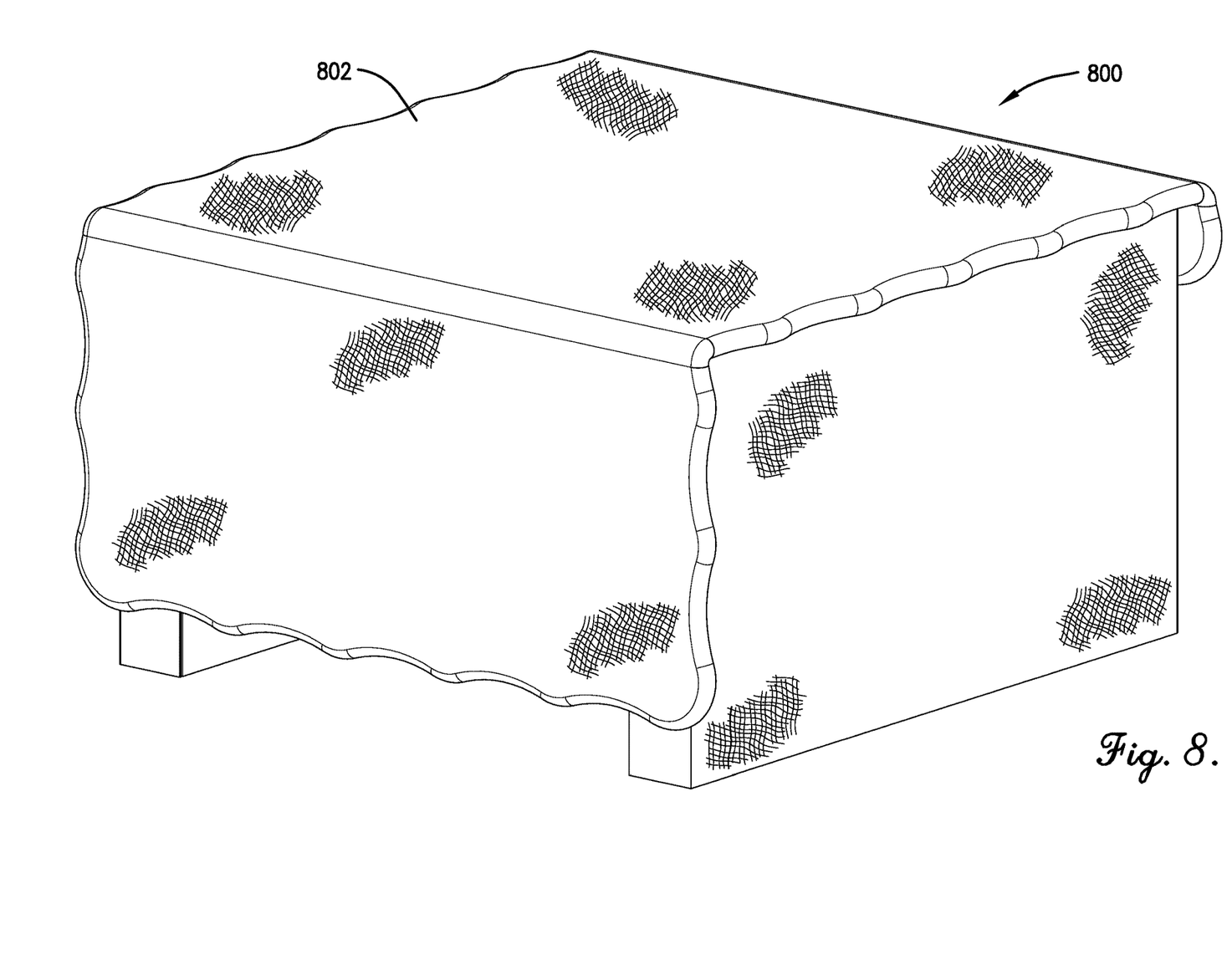
FIG. 8 is a perspective view of an enclosure constructed according to a fourth embodiment of the present invention.
Figure 9:
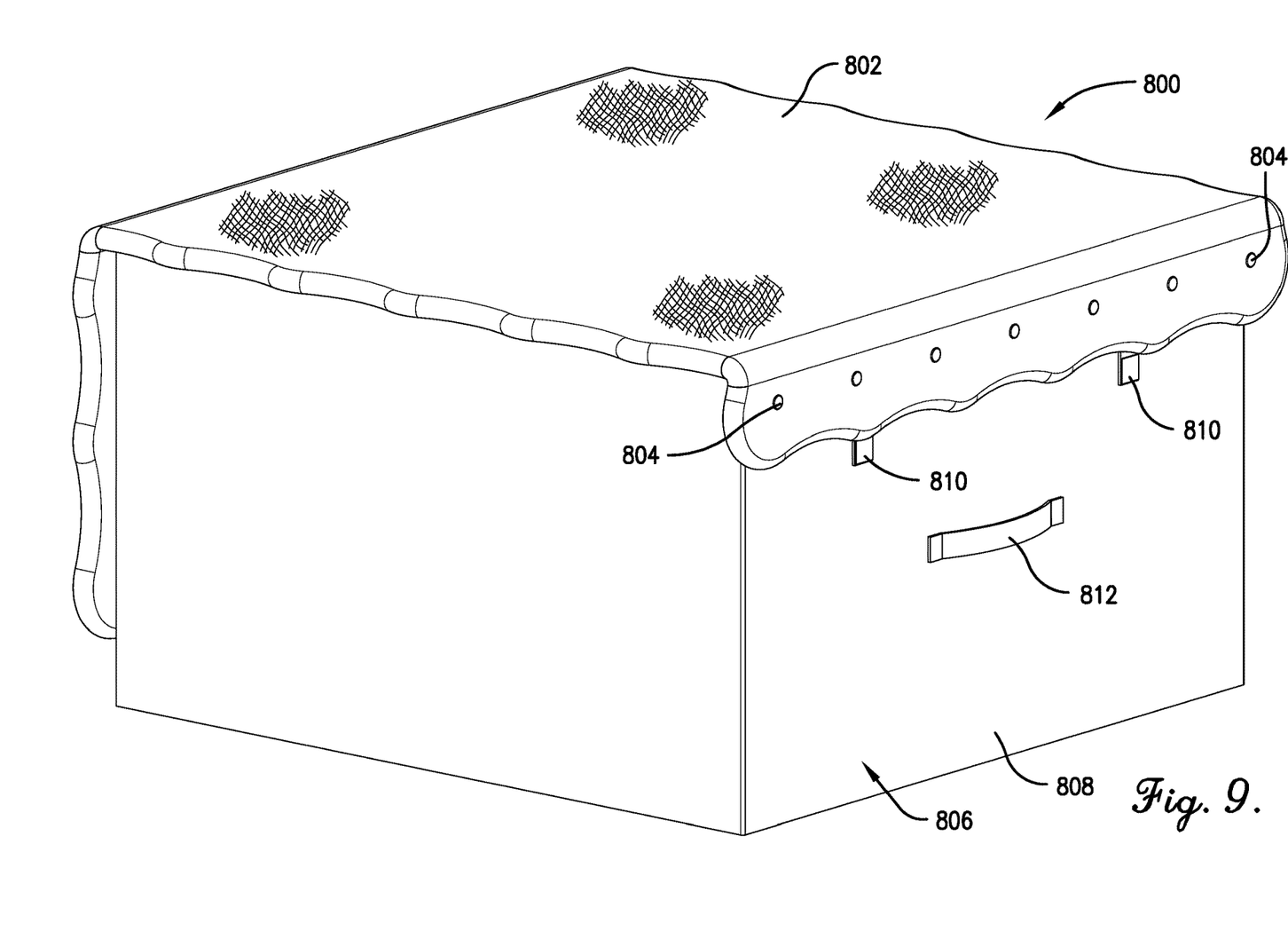
FIG. 9 is a perspective view of the enclosure taken from an opposite angle from FIG. 8 to show exterior sides of a side panel and header panel of the fourth embodiment.

A fourth embodiment comprising enclosure 800 is illustrated in FIGS. 8-9. The enclosure 800 includes a thickened cover 802 extending over a top margin of the enclosure 800, the enclosure 800 being of a similar form factor to the enclosure 10. Turning more particularly to FIG. 9, the cover 802 includes embedded female snap fastener portions 804. The enclosure 800 also includes a header panel 806 with an exterior face 808. Complementary male snap fastener portions (not shown) are embedded in and/or fixed to the exterior face 808. Tabs 810 are also fixed to the exterior face 808. The cover 802 may be removably fixed to the header panel 806 by attaching the female snap fastener portions 804 to the male snap fastener portions. Where the cover 802 is rolled and/or collapsed in the proximity of the header panel 806, the tabs 810 may be wrapped around and may encircle the cover 802 to secure it for stowage and against unintentional redeployment. The enclosure 800 also includes a handle 812 fixed to the exterior face 808 for ease of carrying.

Preferably, the cover 802 is removeable, as noted above, permitting use of interchangeable covers for customization according to personal preferences of the individual. The cover 802 may comprise materials sufficiently permeable to gases to be considered "breathable" fabric.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. An enclosure comprising:
    one or more panels together defining a header and two generally opposing sides, the header comprising a header panel of the one or more panels and the two generally opposing sides respectively comprising first and second side panels of the one or more panels, with the header being attached to the first and second side panels at respective hinges, each of the hinges being configured to permit rotation of a corresponding one of the first and second side panels about the header at a rotational axis;
    the header and two generally opposing sides defining a reclining pocket for receiving a body part of an individual;
    wherein at least one of the one or more panels conforms to a dampened panel construction, the dampened panel construction comprising a cushion layer and a sound absorbing layer having an interior side, with the cushion layer being disposed along and at least partly overlapping the interior side of the corresponding sound absorbing layer;
    the sound absorbing layer exhibiting a greater sound absorption coefficient than the corresponding cushion layer.

2. The enclosure of claim 1, the dampened panel construction further comprising a second sound absorbing layer, wherein—
    the second sound absorbing layer comprises a low-frequency sound absorption material having a sound absorption coefficient at or above five-tenths (0.5) for sound having a frequency within a low range;
    the sound absorbing layer comprises a high-frequency sound absorption material having a sound absorption coefficient at or above nine-tenths (0.9) for sound having a frequency in a high range, the high range being above the low range.

3. The enclosure of claim 2, wherein the low range is between one hundred and twenty-five and two hundred and fifty Hertz (125-250 Hz), inclusive, and the high range is above five hundred Hertz (500 Hz) and at or below five thousand Hertz (5,000 Hz).

4. The enclosure of claim 1, the dampened panel construction further comprising a casing enclosing the cushion layer and the sound absorbing layer.

5. The enclosure of claim 4, further comprising a speaker.

6. The enclosure of claim 5, wherein the speaker is at least partly embedded in the cushion layer of a corresponding one of the one or more panels that conform to the dampened panel construction.

7. The enclosure of claim 6, wherein—
the speaker includes an interior side,
the casing of the corresponding panel covers the interior side of the speaker,
the casing of the corresponding panel comprises a material exhibiting a sound absorption coefficient of less than five tenths (0.5) at all frequencies between two hundred and fifty and two thousand Hertz (250-2,000 Hz), inclusive.

8. The enclosure of claim 1, further comprising a cover attached to the header.

9. The enclosure of claim 8, wherein the cover is detachably attached to the header.

10. The enclosure of claim 8, further comprising tabs fixed to the header and configured to encircle and secure the cover in a collapsed or rolled configuration.

11. The enclosure of claim 1, wherein—
the at least one panel conforming to the dampened panel construction includes the header panel and the first and second side panels.

12. The enclosure of claim 1, wherein—
the header panel includes an interior face and an exterior face,
a first hinge of the hinges is fixed to the first side panel and to the header panel nearer to the interior face than to the exterior face,
a second hinge of the hinges is fixed to the second side panel and to the header panel nearer to the exterior face than to the interior face,
the first hinge and the first side panel are configured so that the first side panel may be placed into a stowed configuration by rotating the first side panel about the first hinge to bring the first side panel into a generally abutting relationship with the interior face of the header panel,
the second hinge and the second side panel are configured so that the second side panel may be placed into a stowed configuration by rotating the second side panel about the second hinge to bring the second side panel into a generally abutting relationship with the exterior face of the header panel.

13. The enclosure of claim 12, wherein the header panel includes a handle fixed to an exposed surface of the header panel between the interior face and the exterior face.

14. The enclosure of claim 12, wherein—
the header panel includes a first side face adjacent the first side panel and a second side face adjacent the second side panel,
the first side panel includes a first end face adjacent the first side face of the header panel,
the second side panel includes a second end face adjacent the second side face of the header panel,
the first end face of the first side panel and the first side face of the header panel are configured to substantially prevent rotation of the first side panel about the first hinge to bring the first side panel into a generally abutting relationship with the exterior face of the header panel,
the second end face of the second side panel and the second side face of the header panel are configured to substantially prevent rotation of the second side panel about the second hinge to bring the second side panel into a generally abutting relationship with the interior face of the header panel.

15. The enclosure of claim 12, further comprising a stowing strap fixed to the header panel and having two free ends, the stowing strap being configured to encircle the first and second side panels and the two free ends being configured for attachment to one another to secure the first and second side panels against the header panel in the stowed configuration.

16. The enclosure of claim 1, wherein the hinges comprise strips of fabric fixed to respective opposite sides of the header panel, each of the hinges also being fixed to a corresponding one of the first and second side panels.

17. The enclosure of claim 1, wherein each of the side panels has a top, further comprising a rod fixed to and extending between the top of the first side panel and the top of the second side panel.

18. The enclosure of claim 17, wherein the rod includes opposing ends, further comprising a base fixed to each of the tops of the first and second side panels, each base being configured for attachment to a corresponding end of the opposing ends of the rod.

19. The enclosure of claim 1, further comprising a pocket attached along an interior of the one or more panels, the pocket being configured to receive at least one electronic device.

20. The enclosure of claim 1, further comprising an electric light fixed to an interior of the one or more panels.

* * * * *